United States Patent [19]
Kazimir et al.

[11] Patent Number: 6,054,595
[45] Date of Patent: Apr. 25, 2000

[54] METHOD FOR SYNTHESIS OF N-HOMOCYSTEINE THIOLACTONYL RETINAMIDE

[75] Inventors: Michal Kazimir, Roseau, Dominica; F. Ray Wilson, II, Waco, Tex.

[73] Assignee: Baylor University, Waco, Tex.

[21] Appl. No.: 09/340,496

[22] Filed: Jun. 30, 1999

[51] Int. Cl.$^7$ .................................................. C07D 333/32
[52] U.S. Cl. .................................................... 549/63
[58] Field of Search ................................................ 549/63

[56] References Cited

U.S. PATENT DOCUMENTS

| | | | |
|---|---|---|---|
| 4,255,443 | 3/1981 | McCully | 424/275 |
| 4,383,994 | 5/1983 | McCully | 424/245 |
| 4,618,685 | 10/1986 | McCully | 549/63 |
| 4,925,931 | 5/1990 | McCully | 536/25 |

OTHER PUBLICATIONS

McCully et al., "Homocysteine and lipid metabolism in atherogenesis: effect of the homocysteine thiolactonyl derivatives, thioretinaco and thioretinamide," *Atherosclerosis*, 83:197–206, 1990.

McCully, "Homocysteine thiolactone metabolism in malignant cells," *Cancer Research*, 36: 3198–3202, 1976.

McCully and Clopath, "Homocysteine compounds which influence the growth of malignant neoplasm," *Chemotherapy*, 23:44–49, 1997.

McCully and Vezeridis, "Antineoplastic activity of a rhodium trichloride complex of oxalyl homocysteine thiolactone" *Cancer Investigation*, 5: 25–30; 1987.

McCully and Vezeridis, "Antineoplastic activity of N–maleamide homocysteine thiolactone amide encapsulated within liposomes," *Proceedings of the Society of Experimental Biology and Medicine*, 180: 57–61; 1985.

McCully and Vezeridis, "Chemopreventive and antineoplastic activity of N–homocysteine thiolactonyl retinamide," *Carcinogenesis*, 8(10):1559–1562; 1987.

McCully and Vezeridis, "Chemopreventive effect of N–homocysteine thiolactonyl retinamido cobalamin on carcinogenesis by ethyl carbamate in mice," *Proceedings of the Society for Experimental Biology and Medicine*, 191: 346–351; 1989.

McCully et al., "Inhibition of neoplastic growth by N–homocysteine thiolactonyl retinamido cobalamin," *Research Communications in Chemical Pathology and Pharmacology*, 66: 117–122; 1989.

McCully et al., "Effect of the synthetic N–homocystein thiolactonyl derivatives, thioretinaco, thioretinamide and thioco on growth and lactate production by malignant cells," *Research Communications in Chemical Pathology and Pharmacology*, 77: 125–128; 1992.

Moon and Itri, "Retinoids and cancer," In: Sporn, M.B., Roberts, A.B., Goodman, D.S. (eds), *The retinoids*. Academic Press, Orlando, FL. 2: 327–371; 1984.

"Peptides: synthesis, structures, and applications," editetd by Bernd Butte. Copyright© 1995 by Academic Press, Inc. San Diego, CA. p. 40–53.

Spindel and McCully, "Conversion of methionine to homocysteine thiolactone in liver," *Biochimica et Biophysica Acta* 343:687–691, 1974.

Sundaresen, "Vitamin A and the sulfate–activating enzymes," *Biochimica et Biophysica Acta*, 113: 95–109; 1966.

*Primary Examiner*—Joseph McKane
*Attorney, Agent, or Firm*—Fulbright & Jaworski L.L.P.

[57] ABSTRACT

The present invention describes a method of organic synthesis for N-homocysteine thiolactonyl retinamide, a compound that has anticancer and antiatherogenic properties.

46 Claims, 5 Drawing Sheets

METHOD FOR SYNTHESIS OF N-HOMOCYSTEINE THIOLACTONYL RETINAMIDE

BACKGROUND OF THE INVENTION

1. Field of the Invention

The present invention relates generally to the fields of organic synthesis of bioactive compounds. More particularly, it concerns the chemical method of synthesis for N-homocysteine thiolactonyl retinamide, a compound that has anticancer and antiatherogenic properties.

2. Description of Related Art

Chemotherapeutic agents such as cyclophosphamide which are commonly used as antineoplastic agents have the disadvantage of cumulative toxicity after prolonged administration in cancer chemotherapy. The subject compound of this invention, N-homocysteine thiolactonyl retinamide, overcomes the disadvantage of toxicity of chemotherapeutic compounds and retinoids, because it is composed of retinoic acid and homocysteine thiolactone bound together in a non-toxic form. Because large doses of N-homocysteine thiolactonyl retinamide can be given without toxicity, the compound is useful for chemoprevention and chemotherapy of malignant neoplasms in animals and for use as an anti-atherogenic agent.

Homocysteine thiolactone is produced naturally in the liver as a metabolite of the essential amino acid, methionine (Spindel and McCully, 1974). Anticancer properties have been demonstrated for several homocysteine thiolactone derivatives (U.S. Pat. Nos. 4,255,443; 4,383,994; 4,618,685; McCully and Vezeridis 1985; McCully and Vezeridis 1987a, b; McCully and Clopath, 1977; McCully 1976; McCully, 1994b).

Retinoids are another group of chemicals which have been demonstrated to have chemopreventive activity against a variety of carcinogens (Moon & Itri, 1984). They are also needed in the reaction of homocysteine with oxygen (Sundaresen, 1966). These observations supported the rational of conjugating homocysteine thiolactone with retinoic acid in an N-substituted fashion to examine its influence on cancerous cells. The synthesis of N-homocysteine thiolactonyl retinamide (also called thioretinamide) from homocysteine thiolactone free base and retinoic acid was attempted by McCully in U.S. Pat. No. 4,618,685.

In general, the procedure described in U.S. Pat. No. 4,618,685 by McCully in 1986, incorporated herein by reference, involves the conjugation of homocysteine thiolactone to retinoic acid using dicyclohexylcarbodiimide as a coupling agent. As specifically described in that patent, the process starts with the preparation of the free base of homocysteine thiolactone and involves the dissolution of 1.01 g of sodium hydroxide in 25 ml water, followed by the addition of 100 ml of methylene chloride, accompanied with rapid mixing, and the further addition of 3.84 g of homocysteine thiolactone hydrochloride slowly to the mixture. After 15 minutes of mixing, the methylene chloride layer is separated, dried over anhydrous sodium sulfate and the solvent is evaporated under reduced pressure at 37° C. 1.17 g (10 mmoles) of the resulting clear liquid (homocysteine thiolactone free base) is immediately added to 50 ml of tetrahydrofuran (or any other non-polar solvent) containing 3.00 g (10 mmoles) of all-trans-retinoic acid. Then, 2.06 g (10 mmoles) of dicyclohexylcarbodiimide is added, and the reaction mixture is stirred 16 hours at 20° C., protected from light. The tetrahydrofuran is removed at 37° C. under reduced pressure, and the yellow-white residue is added to 500 ml of water and 500 ml of ethyl acetate. The mixture is stirred vigorously for one hour, and the ethyl acetate layer is separated and dried over anhydrous sodium sulfate. The ethyl acetate is concentrated to about 20 ml at 50° C. under reduced pressure and cooled. 2.75 g of yellow powder (N-homocysteine thiolactonyl retinamide) represents 69% of theoretical yield. m.p. 172° C. Analysis: C, calculated, 72.2; found, 71.99, corresponds to $C_{24}H_{33}NSO_2$. NMR 60 MHz multiplets 1.1–2.2, triplet 6.3, singlet 7.2 ppm.

Unfortunately, it has recently been shown that the method used to produce homocysteine thiolactonly retinamide in U.S. Pat. No. 4,618,685 does not produce the desired compound in pure form. The inventors of the present invention attempted the method of U.S. Pat. No. 4,618,685, and McCully and Vezeridis, 1987a, and were unsuccessful in obtaining sufficient, pure thioretinamide as confirmed by subsequent analysis by 300 MHz N.M.R. Proton N.M.R. analysis of the compounds produced by McCully's method clearly showed production of dicyclohexylurea (DCU), an unwanted byproduct of the reaction and hence the purity of thioretinamide produced was reduced. In sum, the procedure described in the above-listed references did not produce thioretinamide in the expected quantity or purity.

Despite the difficulties in synthesizing thioretinamide following the procedures described in the McCully patent, the work of McCully showed that there was promise for thioretinamide as a therapeutic. The "thioretinamide" synthesized as described was able to counteract the carcinogenecity of ethyl carbamate in pulmonary neoplasms of strain A female mice. Thioretinamide decreased the number of tumors formed to 80% at doses of 50 mg/week, and 60% at doses of 200 mg/week. Unfortunately, the 200 mg/week mice showed significant weight loss (McCully and Vezeridis, 1987a). Additionally, in U.S. Pat. No. 4,925,931, incorporated herein by reference, thioretinamide has been shown to react with cobalamin to form N-homocysteine thiolactonyl retinamido cobalamin, also known as thioretinaco. Both thioretinamide and thioretinaco have anticarcinogenic and antineoplastic activities, as reported in McCully and Vezeridis, 1987a and McCully and Vezeridis, 1989. In experiments with cultured malignant and normal cells, thioretinaco was found to have antiproliferative activity, and thioco, the complex of homocysteine thiolactone and cobalamin, was found to increase growth of both malignant and normal cells, as reported in McCully et al., 1992. Intra-tumoral administration of thioretinaco decreased the growth of human pancreatic adenocarcinomas in athymic mice, as reported in McCully et al., 1989.

The above-described studies and patents point to great promise for thioretinamide as a chemotherapeutic agent. However, in order to fully realize the potential of this agent, a method of producing it in sufficient quantities and purity is needed. Thus, there is need for the development of methods that produces high yields of pure N-homocysteine thiolactonyl retinamide.

SUMMARY OF THE INVENTION

The present invention presents a method of organic synthesis of N-homocysteine thiolactonyl retinamide, which has a good yield and wherein the compound produced is substantially pure, thereby deficiencies existing in the art are overcome by the present invention. The reaction is prepared in one container in which homocysteine thiolactone is prepared "in situ" and a retinoic acid moiety is added directly to the same reaction mixture to obtain homocysteine thiolactonly retinamide, making the procedure more efficient. The synthesized product is analyzed for purity and yield by using 300 MHz N.M.R. and mass spectroscopy.

An important embodiment of the invention describes a method for the synthesis of N-homocysteine thiolactonyl retinamide comprising, conjugating retinoic acid with a homocysteine thiolactone using one or more coupling agents. In a preferred embodiment of the invention, two coupling agents are used for the synthesis of thioretinamide. The homocysteine thiolactone can be DL-homocysteine thiolactone hydrochloride, L-homocysteine thiolactone hydrochloride, D-homocysteine thiolactone hydrochloride or homocysteine thiolactone hydrochloride free base.

In a preferred embodiment of the invention, a coupling agent used to conjugate the retinoic acid with the homocysteine thiolactone is N-ethyl-N'-(3-demethyl-aminopropyl) carbodiimide. In another preferred embodiment of the invention a second coupling agent can be used. In one embodiment, the second coupling agent is 1-hydroxybenzotriazole. In an alternate embodiment of the invention, the second coupling agent can be 3-hydroxy-4-oxo-3,4-dihydro-1,2,3-benzotriazine. In yet another alternate embodiment of the invention, the second coupling agent is benzotriazole-1-yloyxtris(dimethylamino) phosphonium hexafluorophosphate.

In one aspect of the invention, the method is performed under conditions of reduced light. In a related aspect of the invention, the method is performed under an atmosphere of argon.

In one specific embodiment of the invention, the method involves analysis of the end product by nuclear magnetic resonance spectroscopy and mass spectroscopy. In another specific embodiment of the invention, the molecular weight of the N-homocysteine thiolactonyl retinamide synthesized is found to be about 399 by mass spectroscopy analysis. In a preferred embodiment of the invention, the melting point of N-homocysteine thiolactonyl retinamide is in the range of 150° C.–170° C., more preferably 155° C.–165° C. and even more preferably, 157° C.–159° C. and of course this means that the melting point can be any of 150° C., 151° C., 152° C., 153° C., 154° C., 155° C. 157° C., 158° C., 159° C., 160° C., 161° C., 162° C., 163° C., 164° C., 165° C., 166° C., 167° C., 168° C., 169° C. and/or 170° C.

In another important embodiment of the invention, the synthesis yield of N-homocysteine thiolactonyl retinamide is greater than 70% of a calculated theoretical yield. In preferred embodiments of the invention the synthesis yield is greater than or equal to 70% for example, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 95%, 96%, 97%, 98%, 99%, or 100% of a calculated theoretical yield.

In one particular embodiment of the invention, the solvent used to dissolve retinoic acid is N,N-dimethylformamide. In an alternative embodiment of the invention, the solvent used to dissolve retinoic acid is ethyl acetate.

The invention also contemplates a method for the synthesis of thioretinamide using homocysteine thiolactone hydrochloride as the starting material. The invention further describes a method for the synthesis of N-homocysteine thiolactonyl retinamide comprising, obtaining a homocysteine thiolactone hydrochloride; obtaining retinoic acid; and conjugating the homocysteine thiolactone hydrochloride with retinoic acid using two coupling agents. In one aspect of the invention, the homocysteine thiolactone can be DL-homocysteine thiolactone hydrochloride, L-homocysteine thiolactone hydrochloride or D-homocysteine thiolactone hydrochloride. In an important related embodiment of the invention, the conjugating comprises using N-ethyl-N',-(3-demethyl-aminopropyl) carbodiimide and a second coupling agent. In one aspect of the invention, the second coupling agent can be 1-hydroxybenzotriazole. In an alternate aspect of the invention, the second coupling agent can be 3-hydroxy-4-oxo-3,4-dihydro-1,2,3-benzotriazine. In yet another alternate aspect of the invention, the second coupling agent can be benzotriazole-1-yloyxtris(dimethylamino)phosphonium hexafluorophosphate.

The invention also describes a method for the synthesis of N-homocysteine thiolactonyl retinamide which comprises using DL-homocysteine thiolactone hydrochloride as the starting material and conjugating this with retinoic acid using N-ethyl-N'-(3-demethyl-aminopropyl)carbodiimide and a second agent. In one preferred embodiment of the invention the second coupling agent is 1-hydroxybenzotriazole. In an alternate embodiment of the invention, the second coupling agent can be 3-hydroxy-4-oxo-3,4-dihydro-1,2,3-benzotriazine. In yet another alternate embodiment of the invention, the second coupling agent is benzotriazole-1-yloyxtris (dimethylamino) phosphonium hexafluorophosphate.

A preferred embodiment of the present invention uses N-ethyl-N'-(3-dimethylaminopropyl) carbodiimide (EDC) and 1-hydroxybenzotriazole (HOBt) as coupling agents. In another preferred embodiment of the method, the final product is isolated by an aqueous wash using several aqueous solutions to separate out by-products and produce thioretinamide in solution.

It is contemplated that the homocysteine thiolactonly retinamide synthesized by the methods described herein will be used as an antineoplastic agent, a chemopreventive agent, and as an antiatherogenic agent.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

300 mHz proton N.M.R. of Thioretinamide was performed while dissolved in chloroform. N.M.R. signals of homocysteine thiolactone (FIG. 3) and retinoic acid (FIG. 4) are incorporated into the current N.M.R. Downfield shifting of proton signals of amide hydrogen at 4.5 ppm gives evidence that the molecules are conjugated.

Figure 3:
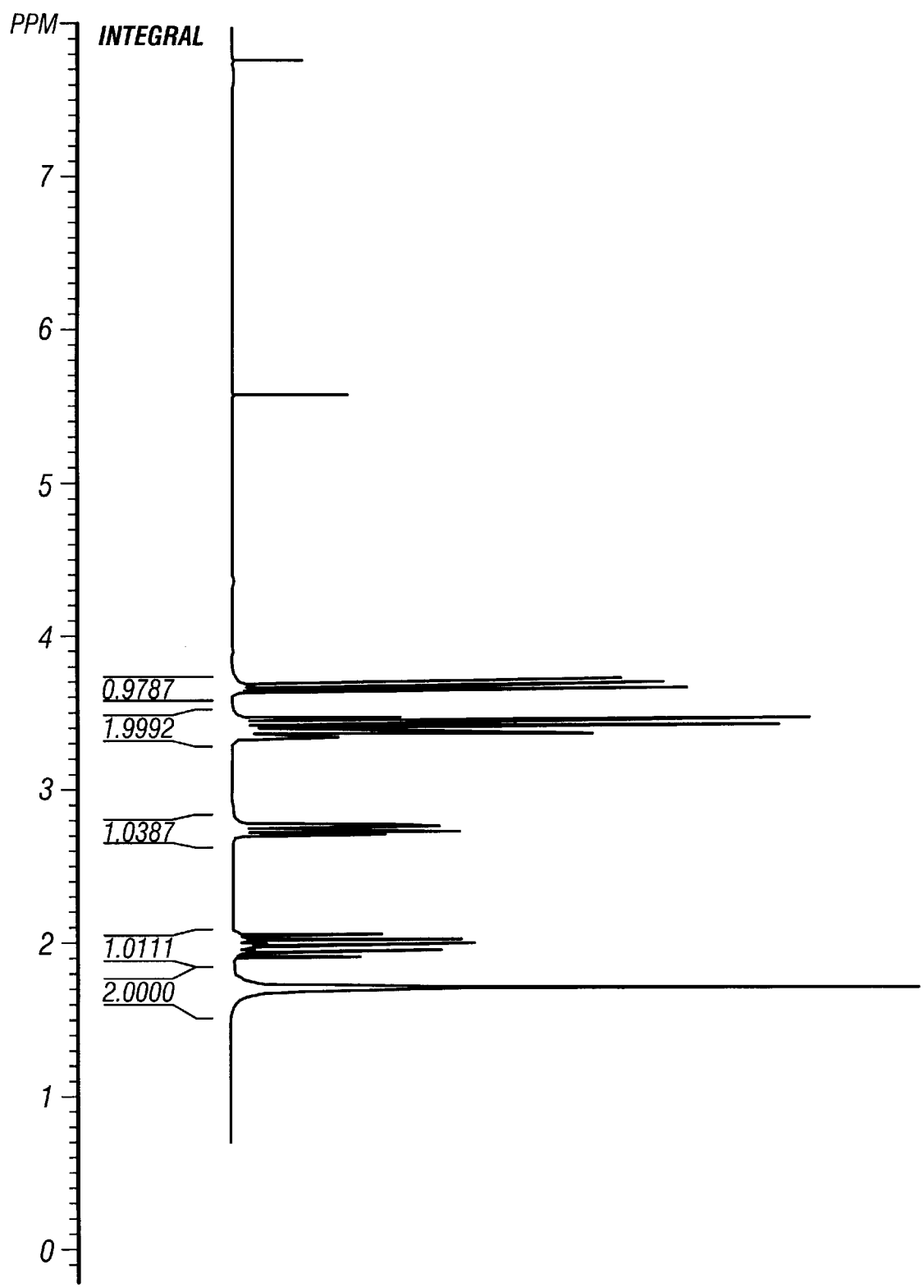

FIG. 3. Proton N.M.R. of homocysteine thiolactone made according to the invention.

300 mHz proton N.M.R. of homocysteine thiolactone performed in the solvent chloroform.

Figure 4:
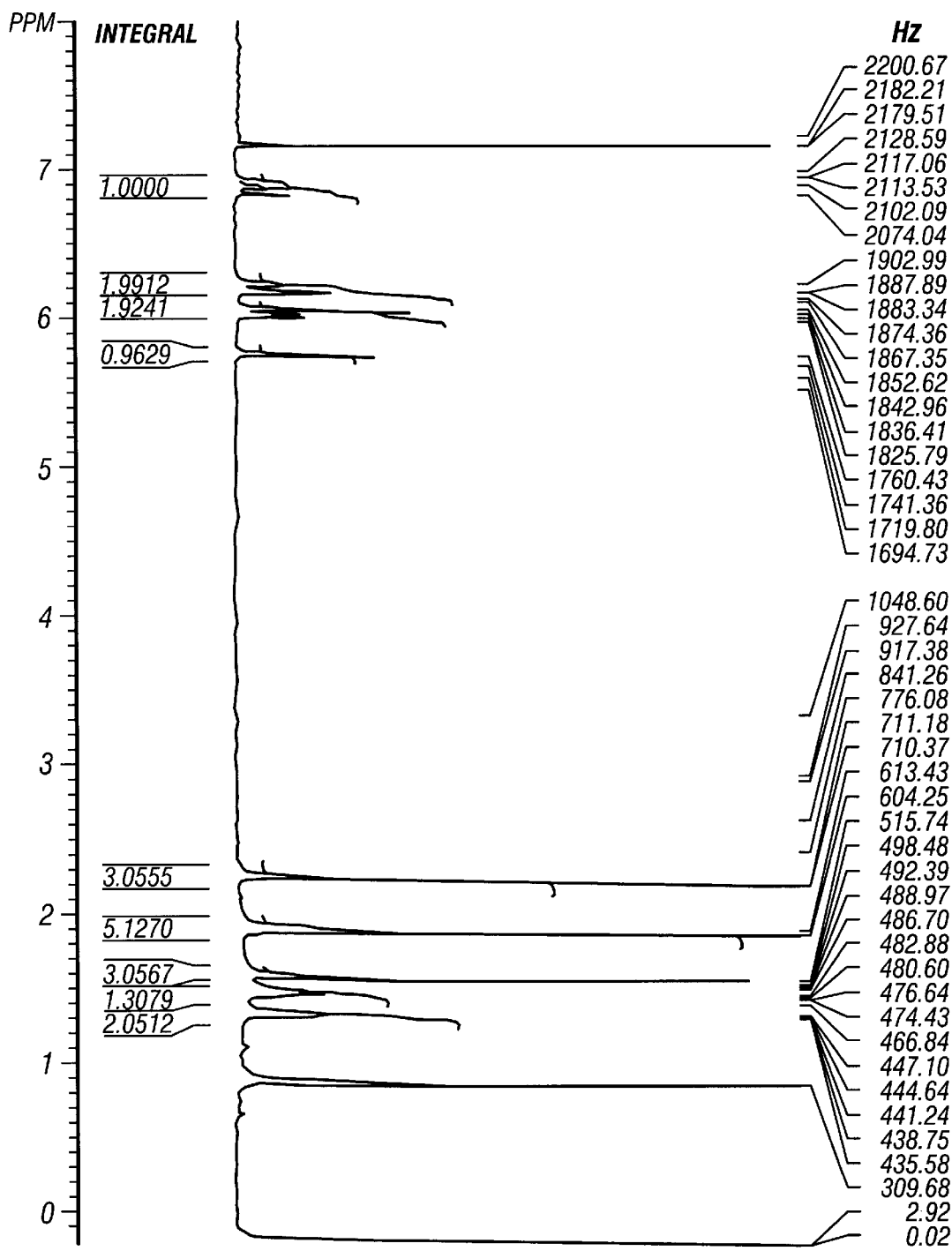

FIG. 4. Proton N.M.R. of retinoic acid. 300 mHz proton N.M.R. of retinoic acid performed in the solvent chloroform.

Figure 5:
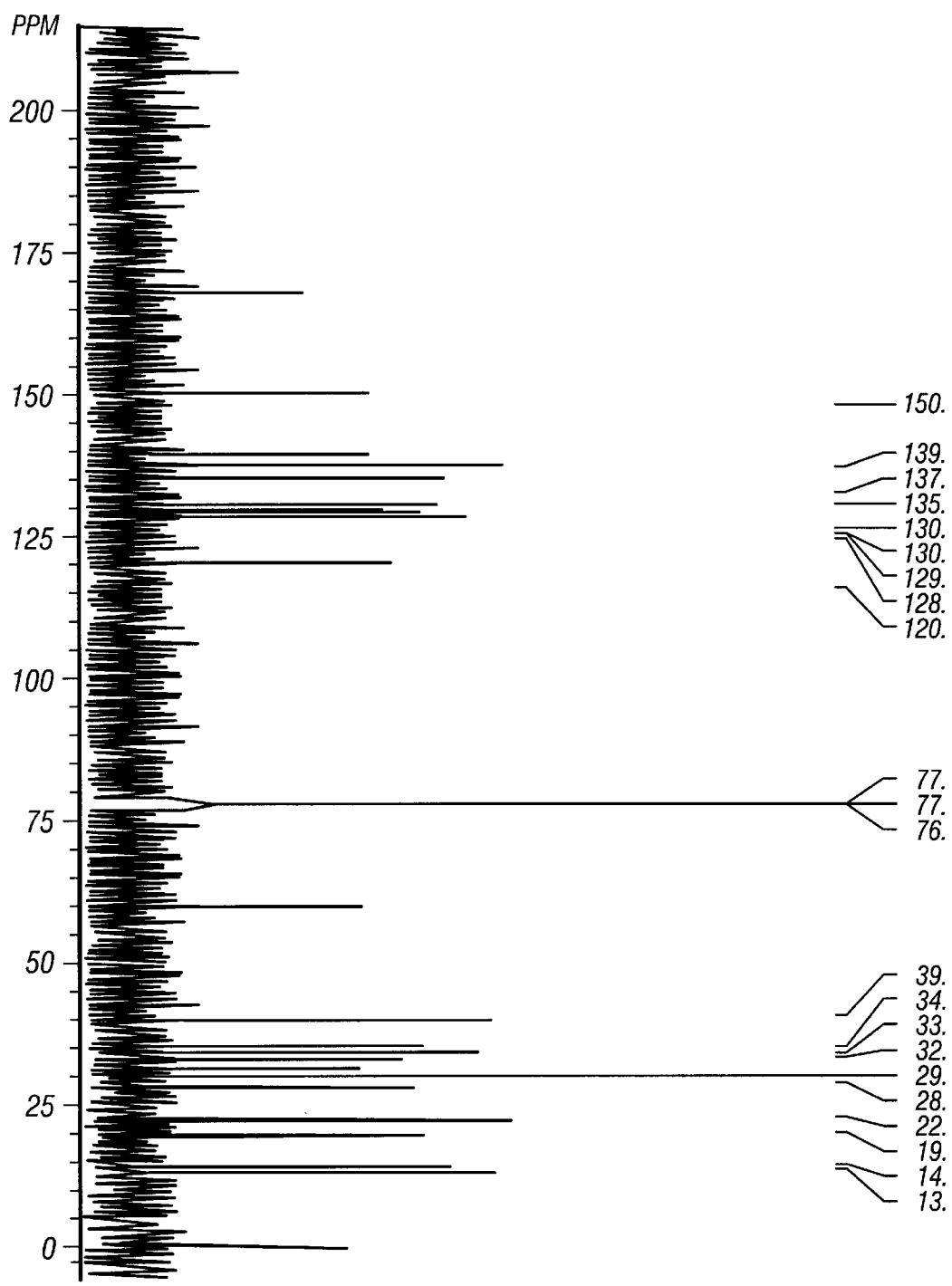

FIG. 5. Carbon N.M.R. of homocysteine thiolactonyl retinamide made according to the invention.

The graph shows 27 peaks that correspond to 24 carbon atoms of thioretinamide and 3 carbon atoms, at approximately 77 ppm, that correspond to the solvent chloroform.

Figure 6:
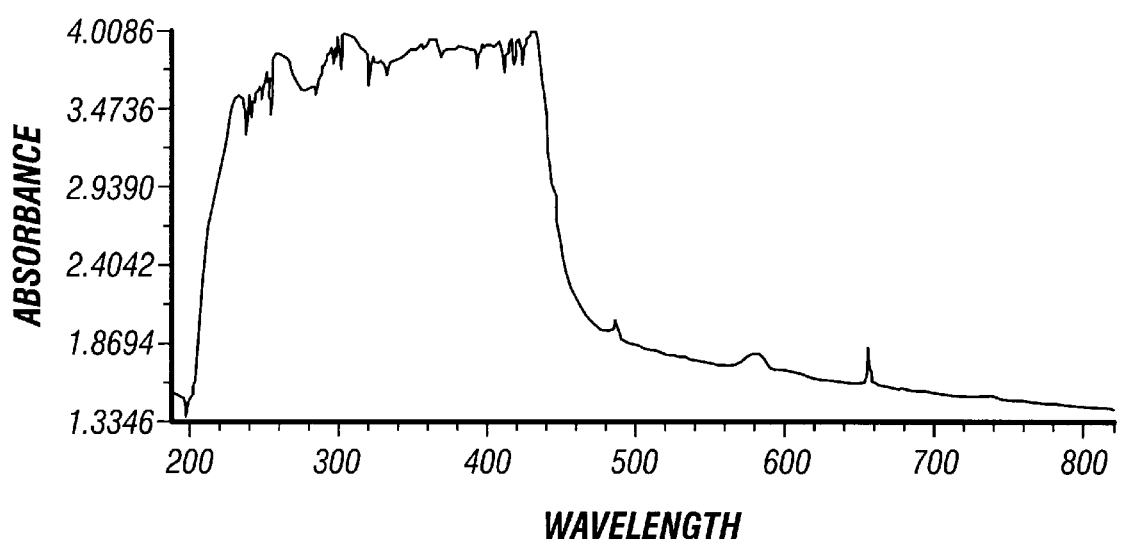

FIG. 6. U.V.-Visible Spectroscopy of Thioretinamide made according to the invention.

DESCRIPTION OF ILLUSTRATIVE EMBODIMENTS

A. THE PRESENT INVENTION

Figure 1:
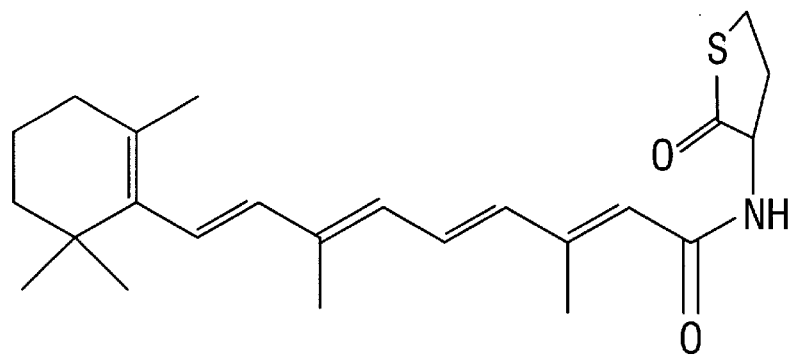
FIG. 1. Structure of homocysteine thiolactonyl retinamide.

The compound produced by the method of this invention is N-homocysteine thiolactonyl retinamide and may be abbreviated to thioretinamide. Thioretinamide has antineoplastic, chemopreventive and antiatherogenic properties. The structure of the thioretinamide (Molecular Formula: $C_{24}H_{33}NO_2S$) is shown in FIG. 1.

The method described in this invention is novel as the activation required to perform the coupling of the homocysteine thiolactone to the retinoic acid is by using N-ethyl-N'-(3-dimethylaminopropyl)carbodiimide (EDC) and 1-hydroxybenzotriazole (HOBt). Furthermore, the homocysteine thiolactone begins in the hydrochloride form and the reaction takes place in one container in which the homocysteine thiolactone is activated for conjugation "in situ" and combines with retinoic acid already present to produce homocysteine thiolactonly retinamide. The method of the present invention uses N-ethyl-N'-(3-dimethylaminopropyl)carbodiimide (EDC) and 1-hydroxybenzotriazole (HOBt) as coupling agents. This produces large quantities of the desired product with few by-products. The final product is isolated by an aqueous wash method which is modified and involves the use of several aqueous solutions to separate out by-products. This produces a thioretinamide solution which does not require crystallization.

B. EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of N-Homocysteine Thiolactonyl Retinamide

The compound produced by methods described in this invention, N-homocysteine thiolactonyl retinamide, is also abbreviated as thioretinamide. This compound is an N-substituted derivative of homocysteine thiolactone which is conjugated to retinoic acid or retinamide. Thioretinamide has antineoplastic, chemopreventive, and antiatherogenic properties. Synthesis of this compound by organic methods allows the investigation of the mechanisms of action of these properties. The steps involved in the synthesis of thioretinamide are as follows:

Synthesis of N-homocysteine thiolactonyl retinamide (thioretinamide) can also be carried out by alternative methods as disclosed herein. Under conditions of reduced light and an atmosphere of argon, all-trans-retinoic acid, 0.666 M (0.200 grams) (Sigma Chemical Co., Missouri), was dissolved in 20 ml of argon protected anhydrous tetrahydrofuran (THF). After stirring ten minutes, the transparent yellow solution was placed in an ice water bath and stirred while the temperature was decreased to 0° C. After stirring at 0° C. for 30 minutes, 1.0 mM (0.1912 grams) of N-ethyl-N'-(3-dimethylaminopropyl)carbodiimide (EDC) (Sigma Chemical Co., St. Louis, Mo.) was added, followed immediately by one mM (0.1350 grams) of 1-hydroxybenzotriazole (HOBt) (Sigma Chemical Co., Missouri). The solution was removed from the ice water bath and heated to 40° C. using oil bath and stirred for three to four hours. (In some preparations, N,N-dimethylformamide (DMF) (Sigma Chemical Co., Missouri) was added drop-wise in order to dissolve all of the EDC and HOBt, but this makes it difficult to separated the final compound from DMF in later steps and yield is compromised.) Two mM of diisopropylethylamine (DIEA) (Sigma Chemical Co., Missouri) (0.2585 grams or 0.35 ml at d=0.7420) was added to the stirring mixture using a syringe. (The solution will be completely dissolved and transparent.) The solution temperature was reduced to 0° C. in an ice water bath and 0.666 mM (0.1026 grams) DL-homocysteine thiolactone hydrochloride was added with rapid mixing. While maintaining protection from light and under an atmosphere of argon, the solution was stirred at 0° C. for 60 minutes followed by gradual temperature increase to 24° C. and stirred for 16 to 20 hours. The solution was subjected to thin layer chromatography at hourly intervals to monitor completion of reaction. Solvent was removed at 37° C. under reduced pressure and the mixture was dried using a vacuum pump aided by a $CO_2$/acetone cooled distillation apparatus. (The resulting powder is yellow in color or an orange/brown viscous residue if DMF is used.)

The non-reacted components of the synthesis were removed using aqueous washes. The mixture was suspended in 12 ml ethyl acetate (EtOAc) (Sigma Chemical Co., St. Louis, Mo.). Aqueous washes were performed using a 50 ml separatory funnel. Separations were performed using 10 ml distilled $H_2O$ (3×), followed by 10 ml of distilled $H_2O$ saturated $NaHCO_3$ (3×), followed by 10 ml of distilled $H_2O$ saturated NaCl (3×), followed by 10 ml of 2 N HCl (3×), and followed by a final wash with 10 ml of distilled $H_2O$ saturated with NaCl. The product was dissolved in the organic layer, which was positioned above the aqueous layer. The organic layer containing thioretinamide was placed in an Erlenmeyer flask and dried over excess sodium sulfate ($Na_2SO_4$) for 2 to 12 hours in the dark at 24° C.

Figure 2:
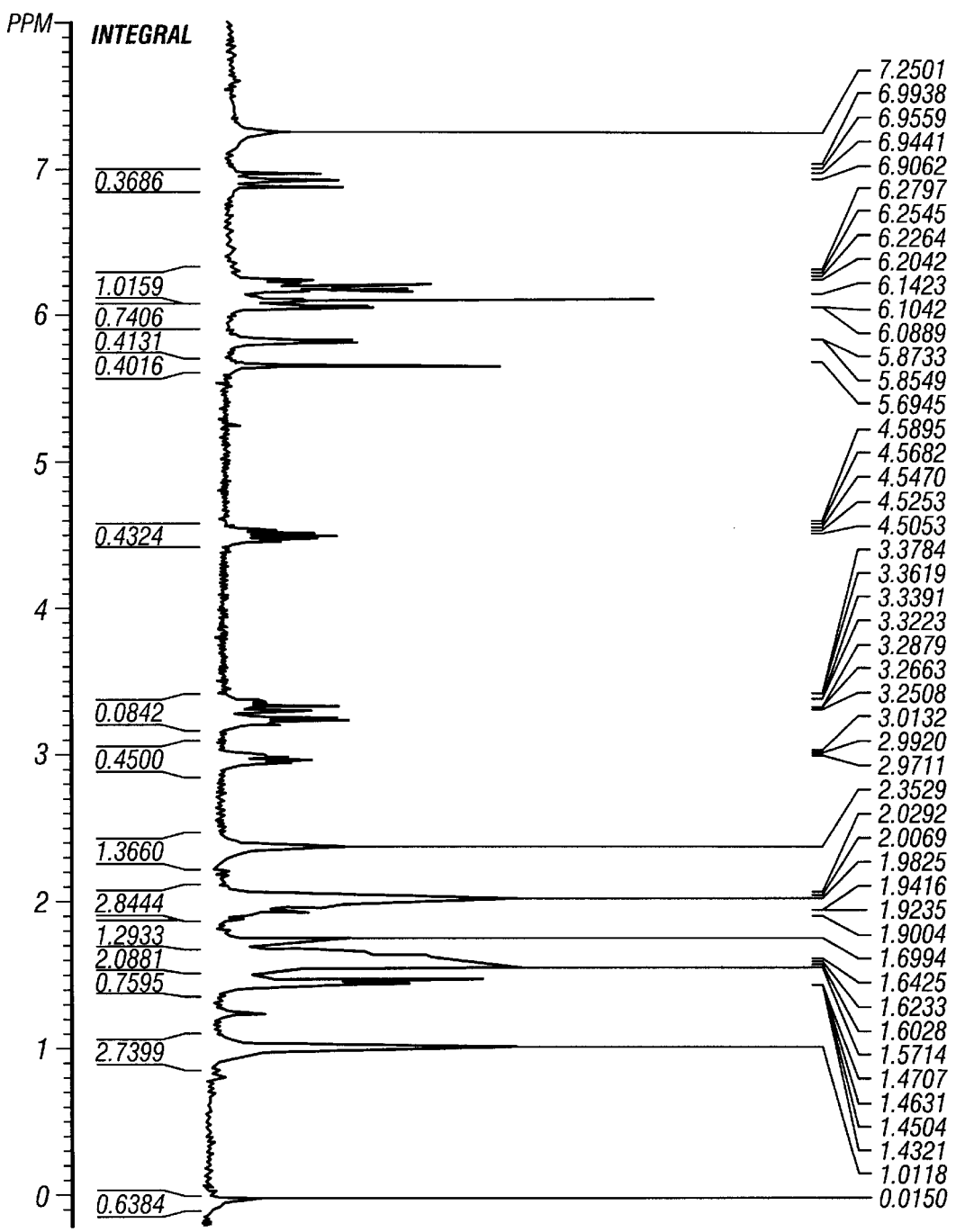
FIG. 2. Proton N.M.R. of homocysteine thiolactonyl retinamide made according to the invention.

Thioretinamide was separated from the sodium sulfate mixture by filtration and purified by recrystalization in EtOAc. The product will be in the form of a yellow crystalline powder. Thioretinamide is a yellow crystal or powder when in pure form. Characterization of thioretinamide was performed using 300 mHz nuclear magnetic resonance spectroscopy (N.M.R.). Thioretinamide was further characterized by mass spectroscopy and melting point determination. The results of the analysis of the thioretinamide produced by these methods is summarized as follows:

300 mHz proton and carbon nuclear magnetic resonance spectroscopy (N.M.R.) (FIGS. 2 and 5)

molecular weight is about 399.22 melting point is about 156–158° C.

synthesis yield is greater than 70% theoretical

The analysis is described in detail in Example 3. Alternative methods of thioretinamide synthesis would differ in respect to the agent used to conjugate or couple the homocysteine thiolactone to the retinoic acid. It is contemplated that the coupling agents may include compounds such as 1,1-carbonyldiimidazole and isopropylcarbodiimidizole. In addition to the solvents tetrahydrofuran, N,N-dimethylformamide, and ethyl acetate used in the synthesis of thioretinamide, the inventors contemplate the use of different non-polar or organic solvents which should not alter the synthesis of thioretinamide.

Thioretinamide produced by the current method has a melting point of 156–158° C. whereas the synthesis used by McCully and Vezeridis, 1987a, had a melting point of 172–173° C. Thus, the compound synthesized by the methods of the present invention is different and has been demonstrated to be in a more pure form by N.M.R. analysis.

Example 2

Modifications for the Synthesis of Thioretinamide

All of the compositions and/or methods disclosed and claimed herein can be made and executed without undue experimentation in light of the present disclosure. While the compositions and methods of this invention have been described in terms of preferred embodiments in Example 1, it will be apparent to those of skill in the art that variations may be applied to the compositions and/or methods disclosed and in the steps or in the sequence of steps of the method described in Example 1 without departing from the concept, spirit and scope of the invention. All such similar substitutes and modifications apparent to those skilled in the art are deemed to be within the spirit, scope and concept of the invention are presented in this Example. For example, the factors can be changed in the procedure described in Example 1, without deviating from the scope of the invention.

Coupling Reagents

Different coupling agents, other than those described in Example 1, may be used to produce thioretinamide. The synthesis of thioretinamide involves a coupling reaction which is an amide-forming reaction between homocysteine thiolactone and retinoic acid. Appropriate activation is required to perform the coupling. Carboxyl activation is the method of choice for the present invention as opposed to amino activation. This example describes alternative activation procedures, reagents, and methods that may also be used to synthesize thioretinamide.

A. Acid Chloride and Fluoride Methods: The amide bond required for the synthesis of thioretinamide can be obtained using acid chlorides or fluorides by treating a homocysteine thiolactone and retinoic acid with either $PCl_5$, $PCl_3$, $SOCl_2$, or $(COCl)_2$.

B. Active Ester Methods: Active esters can be prepared by the dicyclohexylcarbodiimide (DCC) or mixed anhydride method from N-protected amino acids and alcohol. Transesterification methods using trifluoroacetate and trichloroacetate may also be used.

(i) Phenyl Esters: Generally, phenols which have electron-withdrawing substituent in the ortho or para position can be used as active esters. For example, 2,4,5-trichlorophenol, pentachlorophenol, and pentafluorophenol may be used. After the coupling reaction with a phenol-type active ester, the liberated acidic phenol must be removed by an appropriate method (i.e. washing with a aqueous sodium carbonate or recrystalization) as will be apparent to one of ordinary skill in the art.

(ii) N-Hydroxylamine Esters: A series of N-hydroxylamine-type esters represented by N-hydroxysuccinimide (HOSu) ester can be used. HOSu esters are prepared by coupling N-protected amino acids and HOSu by DCC. N-hydroxybenzotriazole (HOBt) esters which are also used in peptide synthesis are prepared using DCC. 3-hydroxy-4-oxo-3,4-dihydro- 1,2,3-benzotriazine (HOOBt) is another alternative reagent to HOBt.

(iii) Bifunctional Active Esters. Various bifunctional active esters such as hydroxyquinoline, catechol, and hydroxypyridine may be used as racemization-free reagents for amide formation between a homocysteine thiolactone and retinoic acid.

C. Unsymmetrical Anhydride Methods:

(i) Mixed Anhydride Method: The mixed anhydride method for amide-bond formation (also used for peptide bond formation) involves aminolysis of an anhydride consisting of an N-protected amino acid and another acid. The carboxylic-carboxylic mixed anhydride method and carbonic-carboxylic mixed anhydride methods can be used. Isobutychloroformate is commonly used for the preparation of carbonic-carboxylic mixed anhydrides.

Mixed anhydrides are also obtained by the reaction of amino acids and dihydroquinoline derivatives (such as, 1-ethoxycarbonyl-2-ethoxy-1,2-dihydroquinoline (EEDQ) or 1-isobutyloxycarbonyl-2-isobutyloxy-1,2-dihydroquinoline (IIDQ)).

(ii) Phosphoric Mixed Anhydride Methods: The mixed anhydrides of amino acids and phosphoric acids are also useful for formation of the peptide bond. The phosphoric reagents that may be used include $(PhO)_2P(O)Cl$ and $Me_2P(S)Cl$. In this category, 3,3'-(chlorophosphoryl)bis( 1,3-oxazolidin-2-one) (BOP-Cl) is particularly useful for coupling of imino acids because of the strong reactivity and selectivity toward the amine component. Norborn-5-ene-2,3,-dicarboximido diphenyl phosphate (NDPP) is another reagent for the active ester-type mixed anhydride method.

D. Carbodiimide Methods: When using carbodiimide, an activated intermediate, which is produced by reaction of a protected amino acid and the carbodiimide, undergoes aminolysis. The reaction of an N-protected amino acid and carbodiimide without an amine component gives another activated species, which also reacts with amine components. Water-soluble carbodiimides such as 1-ethyl-3-(3'-dimethylaminopropyl)carbodiimide have been developed, in such systems, both the reagent and the resulting urea derivative are soluble and easily removable by washing.

E. DCC-Additive Methods: Fragment condensation using DCC and HOSu under strictly controlled conditions preserves the chiral purity almost completely.

F. Azide Methods: The hydrazide is prepared by treating and N-protected amino acid or peptide ester with excess hydrazine hydrate. The hydrazide is converted to azide by tert-butyl or isoamyl nitrite, and the azide reacts with the amine component without extraction with organic solvent.

G. Protected Hydrazide Methods: Peptide esters containing Arg(NO2), Asp(O-t-Bu), Asp(Obzl) (where t-Bu and Bzl represents tert-butyl and benzyl, respectively) cannot be converted to the corresponding hydrazide by hydrazinolysis. In such cases, a protected hydrazide is introduced at the C-terminus of a peptide or carboxyl group of an amino acid. After elongation of the peptide chain, the substituent on the hydrazide is removed, and the resulting hydrazide is converted to an azide. Various protected hydrazides are known in the art. The usual protecting groups for hydrazine are 2, tert-butoxycarbonyl, 2,2,2-trichloroethyloxycarbonyl, and 2,2,2-trichloro-tert-butoxycarbonyl.

(i) Azide Method Using Dephenylphosphorylazide: A free carboxyl group is directly converted to an azide by diphenylphosphorylazice (DPPA). The coupling reaction is considered to proceed via an azide rather than an acyloxyphosphoric mixed anhydride, which is also a likely intermediate. One of skill in the art will recognize that similar reagents such as diethylphosphorocyanidate (DEPC) can be used.

H. Phosphonium and Uronium Salt Type Coupling Reagents: benzotriazole-1-yloyxtris(dimethylamino) phosphonium hexafluorophosphate (bop) is an excellent coupling reagent offering high reactivity and easy handling. The reaction between bop and N-protected amino acid proceeds via an acyloxyphosphonium as an intermediate to produce the corresponding bonzotriazole ester and easily removable by-products such as hexamethylphosphoric triamide (hmpa) and salts. However, hmpa, the starting material the synthesis and a by-product in the reaction of bop, have been reported to have respiratory toxicity. It is therefore contemplated that bop can be replaced by benzotriazole-1-yloxytrspyrrolidinophosphonium hexafluorophosphate (pybop), which as similar reactivity to bop but forms no carcinogenic by-products.

2-(1H-Benzotriazole-1-yl)-oxy-1,3,3-tetramethyluronium hexafluorophosphate HBTU), 2-[2-oxo-1(2H)-pyridyl)-1,1,3,3-bispentamethyleneuronium tetrafluoroborate TOPPipU), and 2-(benzotriazole-1-yl)-oxy-1,3-dimethylimidazolidinium hexafluorophosphate have similar reactivities to BOP. Phosphonium is substituted by uronium in these reagents. 1-hydroxy-7-azabenzotriazole (HOAt), and additive, and 2-(1H-7-azabenzotriazole-1-yl)-oxy-1,1,3,3-tetramethyluronium hexafluorophosphate (HATU), a uronium-type coupling reagent containing the HOAt moiety, enhance the coupling reaction rate and reduce the loss of chiral integrity.

Bromotrispyrrolidinophosphonium hexafluorophosphate (PyBroP) and 2-chloro-1,3-dimethylimidazolidinium hexafluorophosphate have been developed as coupling reagents for N-methylamino acids or a-dealkylamino acids and as esterification reagents.

Group Additions and Deletions

A variation to the method of thioretinamide synthesis could be made, by the addition or temporary deletion of chemical groups (such as methyl groups) or addition or temporary deletion of double bonds in order to protect the molecule during reaction as will be apparent to one of ordinary skill in the art.

Cis/Trans Isomers

Instead of starting with all-trans-retinoic-acid, one of ordinary skill in the art will recognize that one may start with various cis-forms of retinoic acid and have successful synthesis of thioretinamide.

Racemization

The inventors envision the synthesis to include any racemic mixture of homocysteine thiolactone and retinoic acid and any thioretinamide conformation.

Solvents of Reaction

Thioretinamide is soluble in non-polar/organic solvents. A variety of non-polar/organic solvents, generally known to one of ordinary skill in the art, could be used in the synthesis and purification of thioretinamide.

Duration of Reaction

The duration of reactions/procedures listed in the synthesis of thioretinamide in Example 1 are not absolute, but are merely guidelines. A person of skill in the art will appreciate that it is possible to produce thioretinamide in a shorter period of time, or in a longer period of time, than listed in the synthesis method in Example 1. The yield may vary accordingly.

Temperature of Reactions

The temperature of the various stages of synthesis described in Example 1 is not to be regarded as an absolute for successful synthesis of thioretinamide. The skilled artisan will recognize that it is possible to produce thioretinamide at higher and lower temperatures during different steps of the synthesis.

Pressure Conditions of Reaction

The different pressure conditions are not considered as variations in the production of thioretinamide. Reduced pressure was often used to hasten evaporation of solvents, and is not critical to successful synthesis of thioretinamide.

Light Conditions

One of skill in the art will realize that thioretinamide can be synthesized under light conditions that differ from those described in Example 1. Therefore, synthesis should not be considered altered if performed under various light conditions.

Anhydrous Conditions

Thioretinamide synthesis should not be considered altered if performed under various hydrated conditions and this will be appreciated by the skilled artisan.

Separation/Purification Method

Thioretinamide synthesis should not be considered altered if various separation/purification methods are used include among others methods such as, thin layer chromatography, high performance liquid chromatography, aqueous/organic solvent washes, flash chromatography, centrifugal chromatography and recrystalization in various organic solvents known to one of ordinary skill in the art.

Example 3

Analysis of N-Homocysteine Thiolactonyl Retinamide

Verification of thioretinamide synthesis was performed by using proton and carbon N.M.R. and mass spectroscopy. The proton N.M.R. of thioretinamide (FIG. 2) shows both homocysteine thiolactone (FIG. 3) and retinoic acid (FIG. 4) as constituents of thioretinamide. The proton N.M.R. of thioretinamide (FIG. 2) at 1.0–2.4 ppm consists of singlet peaks integrating for the three methyl group hydrogens of the retinoic acid component of thioretinamide. Peaks at 2.9–4.6 ppm correspond to the protons of the homocysteine thiolactone ring of thioretinamide. The peaks at 5.7–7.0 ppm represent the unsaturated protons, vinyl protons, of the retinoic acid component of thioretinamide. The conjugation of homocysteine thiolactone and retinoic acid at the homocysteine thiolaconyl amide is indicated by downfield shifting of proton signals of the amide hydrogen thioretinamide N.M.R. The synthesis of thioretinamide reported by McCully and Vezeridis (1987a) using 60 mHz N.M.R., which reported multiplets 1.1–2.2, triplet 6.3, and singlet 7.2 ppm, does not confirm that thioretinamide was successfully synthesized.

The carbon N.M.R. of thioretinamide (FIG. 5) provided further evidence that thioretinamide was in fact the compound that had been produced. The number of carbon atoms shown by the carbon N.M.R. (27) corresponded to the number of carbon atoms in thioretinamide (24) plus the number of carbon atoms found in the solvent chloroform (3). Identification of carbon atom peaks include the following: Five methyl group carbons are located at 0–30 ppm. Three carbons from the benzene ring and one carbon from the homocysteine thiolactone ring are represented by the four peaks at 30–40 ppm. The non-carboxyl carbon atom located next to the sulfur atom is represented by the peak at 60 ppm. Ten carbon atoms located in the conjugated double bonds of thioretinamide are represented by the peaks at 120–150 ppm. The carboxyl carbon atom of the homocysteine thiolactone ring is represented by the peak at 167 ppm and the carboxyl carbon atom of the retinoic acid back-bone is represented by the peak at 205 ppm. The three peaks at 75–80 ppm represent carbon atoms of the solvent chloroform. Mass spectroscopy results showed that thioretinamide, designated by chemical formula $C_{24}H_{33}NO_2S$ (Table 1 and FIG. 6), had the molecular mass of 399.22320.

The melting point of thioretinamide was determined to be about 156–158° C. This differs from the melting point of 172–173° C. reported by McCully and Vezeridis (1987a).

TABLE 1

Mass Spectroscopy of Thioretinamide

Elemental Composition

File: JAN21EIA Ident: 89 Acq: 21-JAN-1999 16:44:51 +19:39 Cal: JAN21EIA
ProSpecE EI + Magnet BpM: 69 BpI: 1906176 TIC: 16734541 Flags: ACC
Sample Text: SW1 File Text: M. Kazimir, C24H32NSO2, 398.21538
Heteroatom Max: 20 Ion: Both Even and Odd
Limits:

| | | | | | | | | | | | |
|---|---|---|---|---|---|---|---|---|---|---|---|
| 390.983 | 1.0 | | | | | −0.5 | 0 | 0 | 0 | 0 | 0 |
| 401.965 | 100.00 | | | 10.0 | | 30.0 | 50 | 50 | 5 | 10 | 5 |
| Mass | % RA | Pks Std | PPM | mDa | Calc. Mass | DBE | C | H | N | O | S |
| 401.225159 | 5.5 | | −19.0 | −7.6 | 401.217543 | 4.5 | 20 | 33 | | 8 | |
| | | | 19.0 | 7.6 | 401.232800 | 8.5 | 24 | 33 | | 5 | |
| | | | −20.2 | −8.1 | 401.217071 | 4.0 | 19 | 35 | 3 | 2 | 2 |
| | | | 21.2 | 8.5 | 401.233670 | 7.5 | 25 | 37 | | | 2 |
| | | | −22.3 | −9.0 | 401.216201 | 5.0 | 18 | 31 | 3 | 7 | |
| | | | 22.4 | 9.0 | 401.234137 | 13.5 | 25 | 29 | 4 | 1 | |
| | | | 24.1 | 9.7 | 401.234829 | 4.0 | 19 | 35 | 3 | 4 | 1 |
| 400.225822 | 19.2 | | 0.1 | 0.0 | 400.225845 | 8.0 | 25 | 36 | | | 2 |
| | | | 1.2 | 0.5 | 400.226312 | 14.0 | 25 | 28 | 4 | 1 | |
| | | | −2.1 | −0.8 | 400.224974 | 9.0 | 24 | 32 | | 5 | |
| | | | 3.0 | 1.2 | 400.227004 | 4.5 | 19 | 34 | 3 | 4 | 1 |
| | | | −3.7 | −1.5 | 400.224324 | 0.0 | 16 | 36 | 2 | 7 | 1 |
| | | | 4.6 | 1.8 | 400.227654 | 13.5 | 27 | 30 | 1 | 2 | |
| | | | −4.9 | −2.0 | 400.223852 | −0.5 | 15 | 38 | 5 | 1 | 3 |
| | | | −5.5 | −2.2 | 400.223632 | 9.5 | 22 | 30 | 3 | 4 | |
| | | | 6.3 | 2.5 | 400.228346 | 4.0 | 21 | 36 | | 5 | 1 |
| | | | −7.1 | −2.8 | 400.222981 | 0.5 | 14 | 34 | 5 | 6 | 1 |
| | | | −8.4 | −3.3 | 400.222473 | 13.0 | 28 | 32 | | | 1 |
| | | | 8.5 | 3.4 | 400.229217 | 3.0 | 22 | 40 | | | 3 |
| | | | 9.2 | 3.7 | 400.229505 | 0.5 | 15 | 34 | 3 | 9 | |
| | | | 9.6 | 3.9 | 400.229684 | 9.0 | 22 | 32 | 4 | 1 | 1 |
| | | | −10.0 | −4.0 | 400.221822 | 4.0 | 20 | 36 | 2 | 2 | 2 |
| | | | 11.4 | 4.6 | 400.230376 | −0.5 | 16 | 38 | 3 | 4 | 2 |
| | | | −12.2 | −4.9 | 400.220952 | 5.0 | 19 | 32 | 2 | 7 | |
| | | | 12.6 | 5.0 | 400.230848 | 0.0 | 17 | 36 | | 10 | |
| | | | 13.0 | 5.2 | 400.231026 | 8.5 | 24 | 34 | 1 | 2 | 1 |
| | | | −13.3 | −5.3 | 400.220480 | 4.5 | 18 | 34 | 5 | 1 | 2 |
| | | | −15.5 | −6.2 | 400.219609 | 5.5 | 17 | 30 | 5 | 6 | |
| | | | 15.9 | 6.4 | 400.232185 | 5.0 | 18 | 32 | 4 | 6 | |
| | | | −16.7 | −6.7 | 400.219142 | −0.5 | 17 | 38 | 1 | 5 | 2 |
| | | | −16.8 | −6.7 | 400.219101 | 18.0 | 31 | 28 | | | |
| | | | 18.1 | 7.2 | 400.233056 | 4.0 | 19 | 36 | 4 | 1 | 2 |
| | | | −18.4 | −7.4 | 400.218450 | 9.0 | 23 | 32 | 2 | 2 | 1 |
| | | | −18.9 | −7.6 | 400.218272 | 0.5 | 16 | 34 | 1 | 10 | |
| | | | 19.3 | 7.7 | 400.233528 | 4.5 | 20 | 34 | 1 | 7 | |
| | | | −20.0 | −8.0 | 400.217800 | 0.0 | 15 | 36 | 4 | 4 | 2 |
| | | | 21.4 | 8.6 | 400.234398 | 3.5 | 21 | 38 | 1 | 2 | 2 |
| | | | −21.8 | −8.7 | 400.217108 | 9.5 | 21 | 30 | 5 | 1 | 1 |
| | | | −22.2 | −8.9 | 400.216929 | 1.0 | 14 | 32 | 4 | 9 | |
| | | | 22.6 | 9.0 | 400.234865 | 9.5 | 21 | 30 | 5 | 3 | |
| | | | −22.9 | −9.2 | 400.216641 | 3.5 | 21 | 38 | 1 | | 3 |
| | | | 24.3 | 9.7 | 400.235557 | 0.0 | 15 | 36 | 4 | 6 | 1 |
| 399.222427 | 70.9 | | 0.3 | 0.1 | 399.222551 | 0.0 | 16 | 37 | 3 | 4 | 2 |
| | | | −1.4 | −0.6 | 399.221859 | 9.5 | 22 | 31 | 4 | 1 | 1 |
| | | | 1.5 | 0.6 | 399.223023 | 0.5 | 17 | 35 | | 10 | |
| | | | −1.9 | −0.7 | 399.221680 | 1.0 | 15 | 33 | 3 | 9 | |
| | | | 1.9 | 0.8 | 399.223201 | 9.0 | 24 | 33 | 1 | 2 | 1 |
| | | | −2.6 | −1.0 | 399.221392 | 3.5 | 22 | 39 | | | 3 |

A positive ion, accurate mass analysis calculated the mass of thioretinamide ($C_{24}H_{33}NO_2S$) to be 399.223201. Chemical formula and calculated mass is designated by box in Table 1.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods disclosed and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

McCully K S, Olszewski A J, Vezeridis M P Homocysteine and lipid metabolism in atherogenesis: effect of the homocysteine thiolactonyl derivatives, thioretinaco and thioretinamide, *Atherosclerosis,* 83:197–206, 1990.

McCully, K. S. Homocysteine thiolactone metabolism in malignant cells. *Cancer Research,* 36: 3198–3202; 1976.

McCully, K. S. and Clopath, P. Homocysteine compounds which influence the growth of a malignant neoplasm. *Chemotherapy,* 23: 44–49; 1997.

McCully, K. S. and Vezeridis, M. P. Antineoplastic activity of a rhodium trichloride complex of oxalyl homocysteine thiolactone. *Cancer Investigation,* 5: 25–30; 1987b.

McCully, K. S. and Vezeridis, M. P. Antineoplastic activity of N-maleamide homocysteine thiolactone amide encapsulated within liposomes. *Proceedings of the Society of Experimental Biology and Medicine,* 180: 57–61; 1985.

McCully, K. S. and Vezeridis, M. P. Chemopreventive and antineoplastic activity of N-homocysteine thiolactonyl retinamide. *Carcinogenesis,* 8: 1559–1562; 1987a.

McCully, K. S. and Vezeridis, M. P. Chemopreventive effect of N-homocysteine thiolactonyl retinamido cobalamin on carcinogenesis by ethyl carbamate in mice. *Proceedings of the Society for Experimental Biology and Medicine,* 191: 346–351; 1989.

McCully, K. S., Tzanakakis, G. N., and Bezeridis, M. P. Inhibition of neoplastic growth by N-homocysteine thiolactonyl retinamido cobalamin. *Research Communications in Chemical Pathology and Pharmacology,* 66: 117–122; 1989.

McCully, K. S., Tzanakakis, G. N., and Vezeridis, M. P. Effect of the homocysteine thiolactonyl derivatives, thioretinaco, thioretinamide and thioco on growth and lactate production by malignant cells. *Research Communications in Chemical Pathology and Pharmacology,* 77: 125–128; 1992.

Moon, R. C. and Itri, L. M. Retinoids and cancer. In: Sporn, M. B., Roberts, A. B., Goodman, D. S. (eds), The retinoids. Academic Press, Orlando, Fla. 2: 327–371; 1984.

"Peptides: synthesis, structures, and applications," edited by Berud Butte. Copyright© 1995 by Academic Press, Inc. San Diego, Calif. Pp 40–53.

Spindel and McCully, *Biochimica et Biophysica Acta* 343:687–691, 1974.

Sundaresen, P. R. Vitamin A and the sulfate-activating enzymes. *Biochimica et Biophysica Acta,* 113: 95–109; 1966.

U.S. Pat. No. 4,255,443
U.S. Pat. No. 4,383,994
U.S. Pat. No. 4,618,685
U.S. Pat. No. 4,925,931

What is claimed is:

1. A method for the synthesis of N-homocysteine thiolactonyl retinamide comprising, conjugating, in a single reaction mixture, retinoic acid with a homocysteine thiolactone using at least N-ethyl-N'-(3-dimethyl-aminopropyl) carbodiimide and a second coupling agent.

2. The method of claim 1, wherein the homocysteine thiolactone is DL-homocysteine thiolactone hydrochloride.

3. The method of claim 1, wherein the homocysteine thiolactone is L-homocysteine thiolactone hydrochloride.

4. The method of claim 1, wherein the homocysteine thiolactone is D-homocysteine thiolactone hydrochloride.

5. The method of claim 1, wherein the homocysteine thiolactone is homocysteine thiolactone hydrochloride free base.

6. The method of claim 1, wherein said second coupling agent is 1-hydroxybenzotriazole.

7. The method of claim 1, wherein said second coupling agent is 3-hydroxy-4-oxo-3,4-dihydro- 1,2,3-benzotriazine.

8. The method of claim 1, wherein said second coupling agent is benzotriazole-1-yloxytris(dimethylamino) phosphonium hexafluorophosphate.

9. The method of claim 1, wherein the reaction is performed under conditions of reduced light.

10. The method of claim 1, wherein the reaction is performed under an atmosphere of argon.

11. The method of claim 1, further comprising analysis of the product by nuclear magnetic resonance spectroscopy.

12. The method of claim 1, further comprising analysis of the product by mass spectroscopy.

13. The method of claim 1, wherein the molecular weight of N-homocysteine thiolactonyl retinamide is about 399.

14. The method of claim 1, wherein the melting point of N-homocysteine thiolactonyl retinamide is about 156–158° C.

15. The method of claim 1, wherein the synthesis yield of N-homocysteine thiolactonyl retinamide is greater than 70%.

16. The method of claim 1, wherein the solvent used to dissolve retinoic acid is N,N-dimethylformamide.

17. The method of claim 1, wherein the solvent used to dissolve retinoic acid is ethyl acetate.

18. A method for the synthesis of N-homocysteine thiolactonyl retinamide comprising, a) obtaining a homocysteine thiolactone hydrochloride;

b) obtaining retinoic acid; and c) conjugating, in a single reaction mixture, the homocysteine thiolactone hydrochloride with retinoic acid using at least N-ethyl-N'-(3-dimethyl-aminopropyl) carbodiimide and a second coupling agent.

19. The method of claim 18, wherein the homocysteine thiolactone hydrochloride is DL-homocysteine thiolactone hydrochloride.

20. The method of claim 18, wherein the homocysteine thiolactone hydrochloride is L-homocysteine thiolactone hydrochloride.

21. The method of claim 18, wherein the homocysteine thiolactone hydrochloride is D-homocysteine thiolactone hydrochloride.

22. The method of claim 18, wherein said second coupling agent is 1-hydroxybenzotriazole.

23. The method of claim 18, wherein said second coupling agent is 3-hydroxy-4-oxo-3,4-dihydro-1,2,3-benzotriazine.

24. The method of claim 18, wherein said second coupling agent is benzotriazole-1-yloxytris(dimethylamino) phosphonium hexafluorophosphate.

25. The method of claim 18, wherein the reaction is performed under conditions of reduced light.

26. The method of claim 18, wherein the reaction is performed under an atmosphere of argon.

27. The method of claim 18, further comprising analysis of the product by nuclear magnetic resonance spectroscopy.

28. The method of claim 18, further comprising analysis of the product by mass spectroscopy.

29. The method of claim 18, wherein the molecular weight of N-homocysteine thiolactonyl retinamide is about 399.

30. The method of claim 18, wherein the melting point of N-homocysteine thiolactonyl retinamide is about 156–158° C.

31. The method of claim 18, wherein the synthesis yield of N-homocysteine thiolactonyl retinamide is greater than 70%.

32. The method of claim 18, wherein the solvent used to dissolve retinoic acid is N,N-dimethylformamide.

33. The method of claim 18, wherein the solvent used to dissolve retinoic acid is ethyl acetate.

34. A method for the synthesis of N-homocysteine thiolactonyl retinamide comprising, using DL-homocysteine thiolactone hydrochloride as the starting material and conjugating this with retinoic acid using N-ethyl-N'-(3-demethyl-aminopropyl)carbodiimide and a second agent, in a single reaction mixture.

35. The method of claim 34, wherein the reaction is performed under conditions of reduced light.

36. The method of claim 34, wherein the reaction is performed under an atmosphere of argon.

37. The method of claim 34, further comprising analysis of the product by nuclear magnetic resonance spectroscopy.

38. The method of claim 34, further comprising analysis of the product by mass spectroscopy.

39. The method of claim 34 wherein the molecular weight of N-homocysteine thiolactonyl retinamide is about 399.

40. The method of claim 34, wherein the melting point of N-homocysteine thiolactonyl retinamide is about 156–158° C.

41. The method of claim 34 wherein the synthesis yield of N-homocysteine thiolactonyl retinamide is greater than 70%.

42. The method of claim 34, wherein the solvent used to dissolve retinoic acid is N,N-dimethylformamide.

43. The method of claim 34, wherein the solvent used to dissolve retinoic acid is ethyl acetate.

44. The method of claim 34, wherein said second coupling agent is 1-hydroxybenzotriazole.

45. The method of claim 34, wherein said second coupling agent is 3-hydroxy-4-oxo-3,4-dihydro-1,2,3-benzotriazine.

46. The method of claim 34, wherein said second coupling agent is benzotriazole-1-yloxytris(dimethylamino) phosphonium hexafluorophosphate.

* * * * *

UNITED STATES PATENT AND TRADEMARK OFFICE
CERTIFICATE OF CORRECTION

PATENT NO.     :     6,054,595
DATED          :     April 25, 2000
INVENTOR(S)    :     Kazimire et al.

It is certified that error appears in the above-identified patent and that said Letters Patent is hereby corrected as shown below:

On the title page, item [75], line 5, please delete "Dominica" and insert -- Commonwealth of Dominica -- therefor.

On the title page, item [22], line 12, please delete "Jun. 30, 1999" and insert --Jun. 29, 1999 --- therefor.

In claim 34, column 15, line 12, please delete "demethyl-aminopropyl" and insert -- dimethyl-aminopropyl -- therefor.

Signed and Sealed this

Fifteenth Day of May, 2001

Attest:

NICHOLAS P. GODICI

Attesting Officer

Acting Director of the United States Patent and Trademark Office